United States Patent
Petyt et al.

(10) Patent No.: US 8,211,280 B2
(45) Date of Patent: *Jul. 3, 2012

(54) BIOSENSORS AND METHODS OF MAKING

(75) Inventors: Adrian Petyt, Chipping Norton (GB);
Simon Andrew Hector, Swindon (GB)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/876,839

(22) Filed: Sep. 7, 2010

(65) Prior Publication Data

US 2011/0132759 A1    Jun. 9, 2011

Related U.S. Application Data

(63) Continuation of application No. 12/463,201, filed on May 8, 2009, now Pat. No. 7,811,432, which is a continuation of application No. 11/276,432, filed on Feb. 28, 2006, now Pat. No. 7,811,430.

(51) Int. Cl.
*G01N 27/26* (2006.01)

(52) U.S. Cl. ............ 204/403.14; 204/403.01; 204/409; 204/403.04; 205/777.5

(58) Field of Classification Search ..... 204/400–403.15, 204/409; 205/777.5, 778, 792; 600/345–348
See application file for complete search history.

(56) References Cited

U.S. PATENT DOCUMENTS

| | | | |
|---|---|---|---|
| 4,931,404 A | 6/1990 | Kundu | |
| 5,030,310 A | 7/1991 | Wogoman | |
| 5,141,868 A | 8/1992 | Shanks et al. | |
| 5,264,106 A | 11/1993 | McAleer et al. | |
| 5,628,890 A | 5/1997 | Carter et al. | |
| 5,834,626 A | 11/1998 | De Castro et al. | |
| 6,103,033 A | 8/2000 | Say et al. | |
| 6,120,676 A | 9/2000 | Heller et al. | |
| 6,129,823 A | 10/2000 | Hughes et al. | |
| 6,143,164 A | 11/2000 | Heller et al. | |
| 6,241,862 B1 | 6/2001 | McAleer et al. | |
| 6,299,757 B1 | 10/2001 | Feldman et al. | |
| 6,338,790 B1 | 1/2002 | Feldman et al. | |
| 6,436,256 B1 | 8/2002 | Williams et al. | |
| 6,461,496 B1 | 10/2002 | Feldman et al. | |
| 6,551,494 B1 | 4/2003 | Heller et al. | |
| 6,576,101 B1 | 6/2003 | Heller et al. | |
| 6,591,125 B1 | 7/2003 | Buse et al. | |
| 6,592,745 B1 | 7/2003 | Feldman et al. | |
| 6,616,819 B1 | 9/2003 | Liamos et al. | |
| 6,618,934 B1 | 9/2003 | Feldman et al. | |
| 6,719,887 B2 | 4/2004 | Hasegawa et al. | |
| 6,723,371 B2 | 4/2004 | Chih-hui | |
| 6,749,740 B2 | 6/2004 | Liamos et al. | |
| 6,755,949 B1 * | 6/2004 | Bhullar et al. | 204/409 |

(Continued)

FOREIGN PATENT DOCUMENTS

EP    0287883    10/1988

(Continued)

*Primary Examiner* — Jeffrey T Barton
*Assistant Examiner* — Jennifer Dieterle
(74) *Attorney, Agent, or Firm* — Edward J. Baba; Shweta Chandra; Bozicevic, Field & Francis LLP

(57) ABSTRACT

Devices and methods for determining the concentration of an analyte in a sample of liquid are provided.

20 Claims, 3 Drawing Sheets

U.S. PATENT DOCUMENTS

| | | |
|---|---|---|
| 6,764,581 B1 | 7/2004 | Forrow et al. |
| 6,801,041 B2 | 10/2004 | Karinka et al. |
| 6,805,780 B1 | 10/2004 | Ryu et al. |
| 6,863,800 B2 | 3/2005 | Karinka et al. |
| 6,939,450 B2 | 9/2005 | Karinka et al. |
| 6,942,518 B2 | 9/2005 | Liamos et al. |
| 6,942,770 B2 | 9/2005 | Cai et al. |
| 7,058,437 B2 | 6/2006 | Buse et al. |
| 7,086,277 B2 | 8/2006 | Tess et al. |
| 7,563,588 B2 | 7/2009 | Gao et al. |
| 7,811,430 B2 * | 10/2010 | Petyt et al. ............... 204/403.01 |
| 7,811,432 B2 * | 10/2010 | Petyt et al. ............... 204/403.14 |
| 7,905,999 B2 * | 3/2011 | Petyt et al. ............... 204/403.04 |
| 7,922,883 B2 * | 4/2011 | Petyt et al. ............... 204/403.04 |
| 2003/0013147 A1 | 1/2003 | Hildenbrand |
| 2003/0196894 A1 | 10/2003 | Cai et al. |
| 2003/0214304 A1 | 11/2003 | Karinka et al. |
| 2004/0060818 A1 | 4/2004 | Feldman et al. |
| 2004/0206625 A1 | 10/2004 | Bhullar et al. |
| 2004/0225230 A1 | 11/2004 | Liamos et al. |
| 2005/0016844 A1 * | 1/2005 | Burke et al. ............. 204/403.01 |
| 2005/0183494 A1 | 8/2005 | Tess et al. |
| 2005/0278945 A1 * | 12/2005 | Feldman et al. ................. 29/830 |
| 2005/0287035 A1 | 12/2005 | Yon-Hin et al. |
| 2006/0042080 A1 | 3/2006 | Say et al. |
| 2006/0278525 A1 | 12/2006 | Petyt et al. |
| 2007/0199818 A1 | 8/2007 | Petyt et al. |

FOREIGN PATENT DOCUMENTS

| | | |
|---|---|---|
| EP | 0359831 | 3/1990 |
| EP | 0851224 | 7/1998 |
| EP | 1211321 | 6/2002 |
| EP | 1482307 | 12/2004 |
| WO | 2001073109 | 10/2001 |
| WO | 2001073395 | 10/2001 |
| WO | 2005040404 | 5/2005 |

* cited by examiner

BIOSENSORS AND METHODS OF MAKING

CROSS-REFERENCE TO RELATED APPLICATIONS

This application is a continuation application of application Ser. No. 12/463,201 filed on May 8, 2009, now U.S. Pat. No. 7,811,432, which is a continuation application of application Ser. No. 11/276,432, filed Feb. 28, 2006, now U.S. Pat. No. 7,811,430, which are incorporated herein by reference.

BACKGROUND OF THE INVENTION

Biosensors, also referred to as analytical sensors or merely sensors, are commonly used to determine the presence and concentration of a biological analyte in a sample. Such biosensors are used, for example, to monitor blood glucose levels in diabetic patients.

As sensors continue to be used, there continues to be an interest in sensors that are easy to use and manufacture.

SUMMARY OF THE INVENTION

The present disclosure is directed to a biosensor or sensor for determining the concentration of an analyte in a sample of liquid, the biosensor having a sample chamber formed, in part, by an incompressible element, e.g., an incompressible elongate element. Accordingly, embodiments include a sensor having an incompressible element in the sample chamber.

Embodiments of the sensor may include at least one support substrate, an electrode arrangement on the support substrate, a cover substrate positioned over the electrode arrangement, a sample chamber, and an incompressible element in contact with the cover. The incompressible element may extend between the support substrate and the cover substrate. In certain embodiments, the incompressible element may provide an opening in at least one edge of the biosensor, the opening providing access to the sample chamber and the electrode arrangement.

Embodiments of the invention include sensors having sensing chemistry present in the sample chamber, proximate the incompressible element. In some embodiments, the sensing chemistry is carried by the incompressible element, either on the surface thereof or within the body thereof.

In one particular aspect, the disclosure is directed to a biosensor having a sample chamber and an incompressible element in the sample chamber. There may be sensing chemistry proximate the incompressible element, which could include an enzyme and/or a redox mediator.

In another aspect, the disclosure is to a biosensor strip for determining the concentration of an analyte in sample, the biosensor strip having a first substrate, a second substrate in covering relation to the first substrate, and a sample chamber present between the first substrate and the second substrates. An electrode arrangement is present between the first substrate and the second substrate and in the sample chamber. An incompressible element extends between the first side edge and the second side edge of the sensor in the sample chamber and forms an opening between the first substrate and the second substrate at one of the first side edge and the second side edge. There is sensing chemistry proximate the incompressible element. This incompressible element may form the first opening at the first side edge and also may form a second opening between the first substrate and the second substrate at the second side edge, where the first opening may be an inlet and the second opening may be a vent.

In yet another aspect, the disclosure is to a biosensor strip for determining the concentration of an analyte in a sample, the biosensor strip having a first substrate, a second substrate in covering relation to the first substrate, and a first opening between the first substrate and the second substrate at a first side edge of the strip and forming a second opening between the first substrate and the second substrate at a second side edge of the strip. A sample chamber is defined by the first substrate, the second substrate and the first and second openings, and an electrode arrangement is present in the sample chamber. There is at least one filament within the sample chamber, the filament comprising sensing chemistry.

The disclosure is also to a method of providing a sample to a sample chamber of a biosensor, the method comprising contacting a side edge of the biosensor with the sample to provide sample through an opening into the sample chamber, and exposing the sample to sensing chemistry proximate an incompressible element in the sample chamber. The method may include venting the sample chamber via a second side edge of the biosensor.

Another method is provided, a method of manufacturing a sensor, the method comprising positioning an incompressible element on a first substrate, overlying a second substrate over the first substrate and incompressible element to form a layered construction having at least one sample chamber, and converting the layered construction into at least one sensor, each of the at least one sensor having a sample chamber. The converting may be done by separating the layered construction into a plurality of sensors.

DETAILED DESCRIPTION OF THE INVENTION

As summarized above, the present invention is directed to sensors or biosensors that include an incompressible element. "Sensors", "electrochemical sensors", "electrochemical sensor strips", "biosensors", and variations thereof, are devices configured to detect the presence of and/or measure the concentration of an analyte in a sample via electrochemical oxidation and reduction reactions.

As used herein, the phrase "incompressible element" means an element that resists compression. As a non-limiting example, in certain embodiment an incompressible element will not only resist compression by the methods of this invention used to apply the cover to the remaining components of the individual biosensor, but will also resist compression during normal storage and use of the completed biosensor. In those embodiments in which an incompressible element provides one or more vents, the incompressible element need only resist compression to the degree that the vent(s) formed by the element remain open to the atmosphere. Examples of incompressible elements include, but are not limited to, ribbon, filament, a thread, yarn, layer, or the like. The term "filament" means any fine, fiber, generally having a circular or substantially circular cross-section; a filament is generally elongated. A "monofilament" is one type of filament. A thread is a plurality of filaments twisted together. A yarn includes a plurality of threads, generally twisted together. The term "ribbon" means a narrow strip or band of material, typically made of natural material or synthetic material. A ribbon may be made from a plurality of filaments or may be a single filament.

In some embodiments, the sensor includes two substrates, an electrode arrangement, and an incompressible element between the substrates. The surfaces of the substrates, together with the incompressible element, define a sample chamber. The sample chamber has a size suitable for filling.

Figure 1:
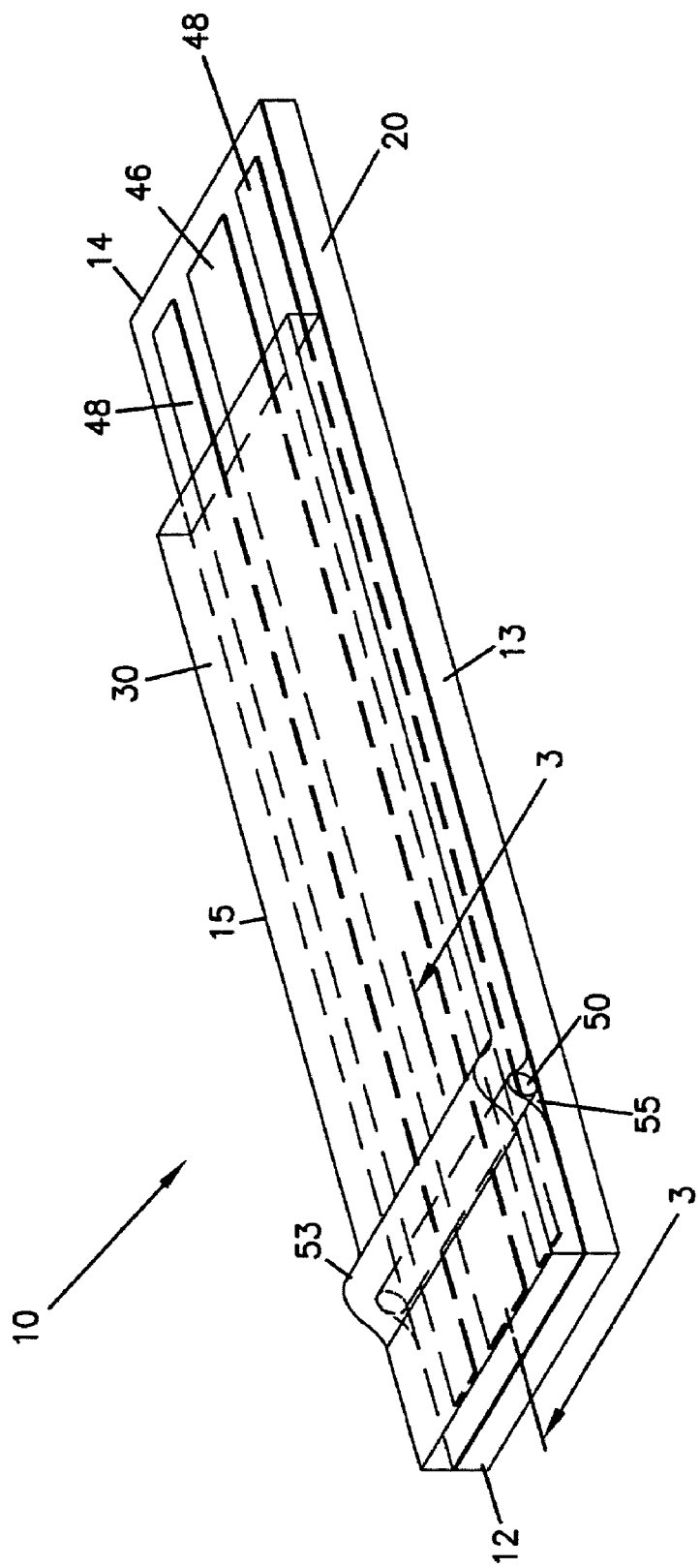
FIG. 1 is a schematic perspective view of an embodiment of a biosensor according to the present invention.
Figure 2:
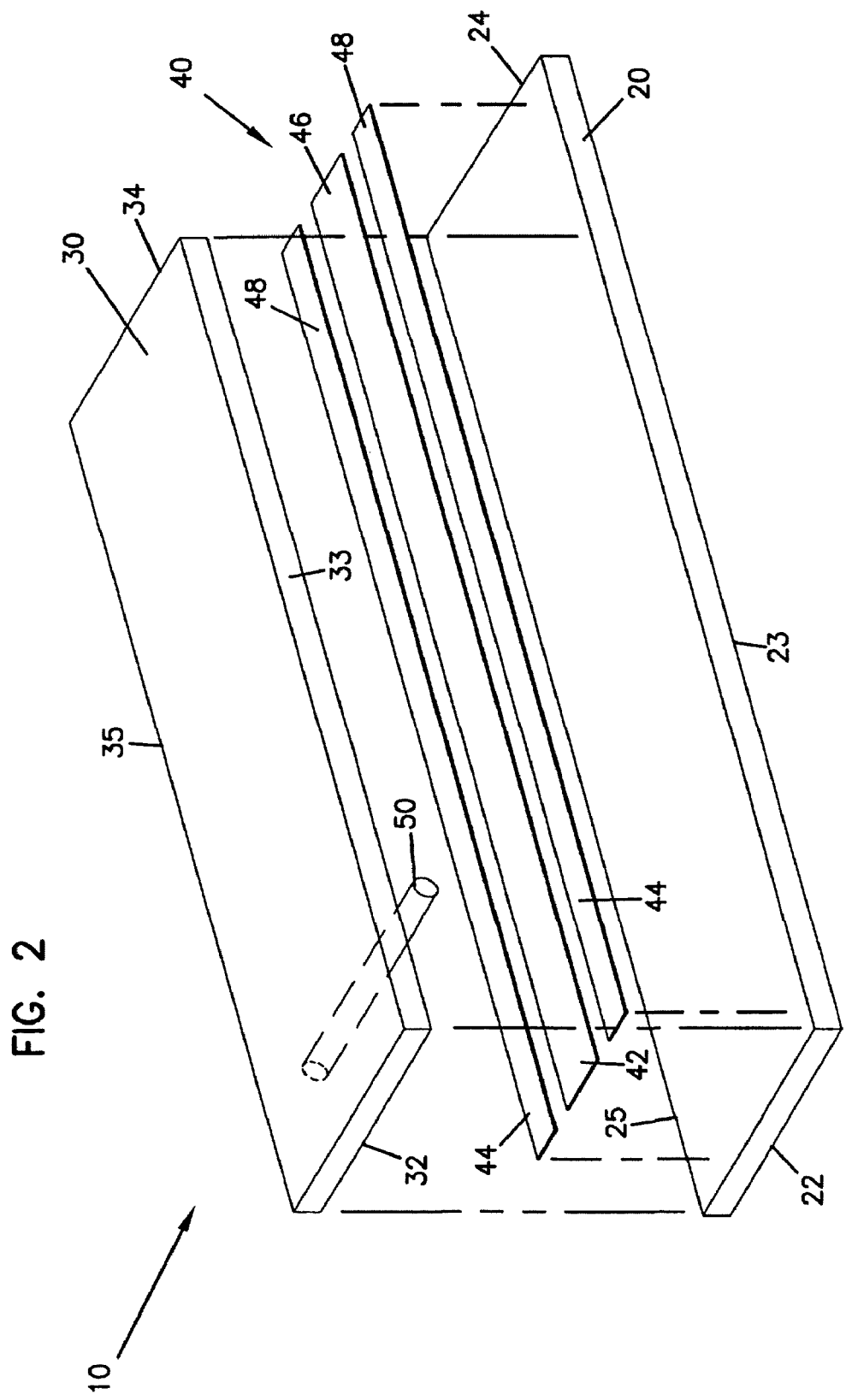
FIG. 2 is an exploded view of the biosensor strip of FIG. 1.
Figure 3:
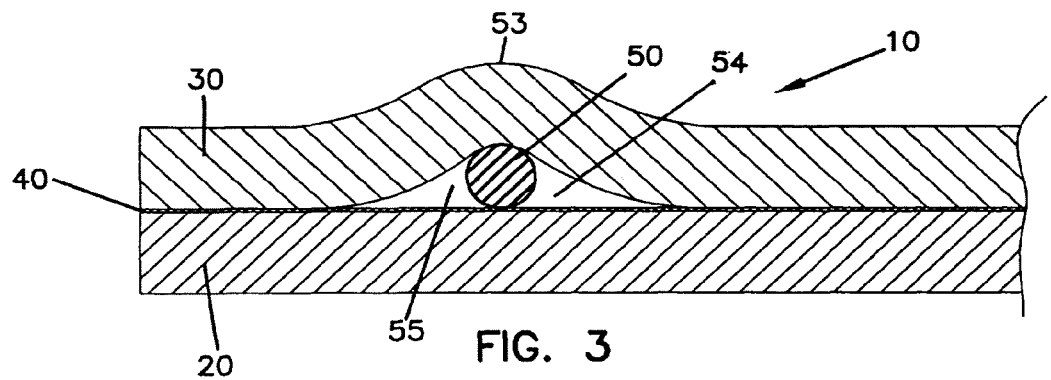
FIG. 3 is a cross-sectional view of the biosensor strip of FIG. 1 taken along line 3-3.

Referring to the Drawings in general and FIGS. 1-3 in particular, a first embodiment of an in vitro electrochemical sensor 10 of the invention is schematically illustrated, and which in this particular embodiment is a small volume sensor strip. Sensor strip 10 has a first substrate 20 with an electrode arrangement 40, a second substrate 30, and an incompressible element 50 therebetween. Together, these elements form a sample chamber 55. The invention is described primarily with respect to an electrochemical sensor strip for exemplary purposes only. It is to be understood that the sensors of the invention may be optical sensors, etc.

Sensor 10 is a layered construction, in this particular embodiment having a generally rectangular shape forming a strip, i.e., its length is longer than its width, although other shapes are possible as well. As will be described below, in one embodiment, electrode arrangement 40 includes at least one working electrode, at least one counter electrode (e.g., two counter electrodes), and optionally, at least one indicator electrode (e.g., two indicator electrodes). In some embodiments, the at least one counter electrode may function as an indicator electrode.

Referring to FIG. 1, sensor 10 has a first end 12, an opposite second end 14, a first side edge 13 and an opposite second side edge 15. First end 12 may be referred to as the "tip" or the "distal end" of sensor 10, and second end 14 may be referred to as the "proximal end".

The length of sensor 10 extends in the longitudinal direction from first end 12 to second end 14. The width of sensor 10 extends laterally across sensor 10 from first edge 13 to second edge 15.

The dimensions of a sensor may vary. In certain embodiments, the overall length of sensor strip 10 from end 12 to end 14 may be no less than about 20 mm and no greater than about 50 mm. For example, the length may be between about 30 and 45 mm, e.g., about 30 to 40 mm. It is understood, however, that shorter and longer sensor strips 10 could be made. In certain embodiments, the overall width of sensor strip 10 from edge 13 to edge 15 may be no less than about 3 mm and no greater than about 15 mm. For example, the width may be between about 4 and 10 mm, about 5 to 8 mm, or about 5 to 6 mm. In one particular example, sensor strip 10 has a length of about 32 mm and a width of about 6 mm. In another particular example, sensor strip 10 has a length of about 40 mm and a width of about 5 mm. In yet another particular example, sensor strip 10 has a length of about 34 mm and a width of about 5 mm.

Substrates

As provided above, sensor strip 10 has first and second substrates 20, 30, non-conducting, inert substrates which form the overall shape and size of sensor strip 10. Substrates 20, 30 may be substantially rigid or substantially flexible. In certain embodiments, substrates 20, 30 are flexible or deformable. In some embodiments, substrate 30 is more flexible than substrate 20, as is explained below.

Examples of suitable materials for substrates 20, 30 include, but are not limited, to polyester, polyethylene, polycarbonate, polyvinyl chloride, polypropylene, nylon, and other "plastics" or polymers. Other non-conducting materials may also be used. One or both of substrates 20, 30 may be or include a transparent portion.

One or both of substrates 20, 30 may include an adhesive coating thereon, or could be an adhesive tape. Having an adhesive coating or layer facilitates the construction of sensor 10 by holding substrates 20, 30 and the other elements together.

Referring to FIGS. 1 and 2, first or bottom substrate 20 has a first end 22, an opposite second end 24, a first side edge 23 and an opposite second side edge 25. Similarly, second or top substrate 30 has a first end 32, an opposite second end 34, a first side edge 33 and an opposite second side edge 35.

The length of substrate 20, 30 extends in the longitudinal direction from first end 22, 32 to second end 24, 34. The width of substrate 20, 30 extends laterally across substrate 20, 30 from first edge 23, 33 to second edge 25, 35. The length and width of substrates 20, 30 may be the same or different, and in many embodiments will be the same. The larger length and width of substrates 20, 30 generally forms the overall length and width of sensor 10.

The thickness of substrates 20, 30 may be the same or different and may vary throughout substrate 20, 30, wherein certain embodiments the thickness may be at least about 0.05 mm and generally no greater than about 3 mm, e.g., between about 0.2 and about 2 mm. In certain embodiments the thickness is about 0.25 mm. It is understood that both shorter and longer lengths for either or both substrate 20 and substrate 30 may be used, as well as wider and/or thicker substrates 20, 30 in certain embodiments. The material and dimensions of substrate 30 may be different from those of substrate 20.

Sample Chamber

Positioned between substrate 20 and substrate 30 is a sample chamber 55 for receiving a volume of sample to be analyzed by sensor 10; see FIGS. 1 and 3. Sample chamber 55 is configured so that when a sample is provided in chamber 55, the sample is in electrolytic contact with both the electrode arrangement, particularly the working electrode and the counter electrode, which allows electrical current to flow between the electrodes to effect the electrolysis (electrooxidation or electroreduction of a compound either directly at an electrode or via one or more electron transfer agents) of the analyte. The sample to be analyzed is present in a measurement zone, which, in some embodiments, is smaller than the sample chamber. Sensor strip 10 is configured to receive a sample into sample chamber 55 via an inlet 54 (see FIG. 3).

Sample chamber 55 includes at least one inlet 54 at an end of sample chamber 55. That is, at least one end of sample chamber 55 is open, and in this embodiment, two ends of sample chamber 55 are open, at edges 13, 15. When two ends of sample chamber 55 are open, one end may provide an inlet to sample chamber 55 and the other end may provide an outlet or vent.

Sample chamber 55 has a volume sufficient to receive a sample of biological fluid for analysis therein. In some embodiments, such as when sensor strip 10 is a small volume sensor, sample chamber 55 has a volume that is no more than about 1 μL, for example no more than about 0.5 μL and also for example, no more than about 0.25 μL. A volume of no more than about 0.1 μL, is also suitable for sample chamber 55, as are volumes of no more than about 0.05 μL and no more than about 0.03 μL. In yet other embodiments, the measurement zone, which has the volume of sample that is interrogated, has a volume that is no more than about 1 μL, for example no more than about 0.5 µL, also for example, no more than about 0.25 µL, or even no more than about 0.1 µL. Volumes of no more than about 0.05 µL and no more than about 0.03 µL are also suitable volumes for a measurement zone. For these measurement zone volumes provided, the volume of sample chamber 55 may be no more than, for example, about 1 µL, or may be greater than about 1 µL.

As noted above, sample chamber 55 is defined by substrate 20, substrate 30 and incompressible element 50. Incompressible element 50 extends through at least a portion of sample chamber 55.

Incompressible Element

Incompressible element 50 is present in sensor 10 between substrate 20 and substrate 30, extending between side edges 23, 33 and 25, 35, for example, laterally across sensor 10 between side edge 13 and side edge 15. Incompressible element 50 may extend to or end short of either or both side edges 13 and 15. For a rectangular sensor strip, in some embodiments incompressible element 50 extends perpendicular to side edges 13, 15 and parallel to end edges 12, 14, however, incompressible element 50 could be positioned at an angle thereto, for example, at angle ranging from about 10 to about 45 degrees to side edges 13, 15; other angles would also be suitable. Although in many embodiments incompressible element 50 extends from side edge 13 to side edge 15 in a straight line, it is possible incompressible element 50 may be curved or have a tortuous path. In another embodiment, incompressible element 50 may extend from end 12 to a side edge 13 or 15. Additionally, in many embodiments, where side edges 13, 15 are parallel, incompressible element 50 extends perpendicular to side edges 13, 15. Additionally or alternatively, for example, the distance from edge 12 to an edge of incompressible element is substantially constant along a dimension (e.g., length) of incompressible element 50. Incompressible element 50 may or may not be tensioned.

Incompressible element 50 may be provided in various forms, such as, for example, a thread, a yarn, a ribbon, a monofilament, a tape, or the like. In some embodiment, incompressible element 50 is composed of at least one filament, and often multiple filaments. Incompressible element 50 may be, for example, a plurality of threads, a plurality of yarns, a plurality of ribbons, a plurality of filaments or monofilaments, or a plurality of tapes. Suitable materials for incompressible element 50 include, but are not limited to, nylon, polyester and other polymeric materials, and natural materials, for example, cotton, wool, and jute.

Incompressible element 50 has sufficient strength and size to form sample chamber 55, specifically, by providing an obstacle between substrate 20 and substrate 30. In other words, incompressible element 50 increases the distance between the opposing surfaces of substrates 20 and 30, i.e., element 50 inhibits substrate 30 from lying in close contact with substrate 20 in the area proximate incompressible element 50.

In many embodiments, incompressible element 50 typically has a dimension (e.g., diameter or width) that is at least about 0.01 mm. Also in many embodiments, incompressible element 50 has a dimension that is no more than about 5 mm. In some embodiments, incompressible element is about 0.05 mm to about 2 mm in a dimension, e.g., about 0.08 to about 1 mm. Specific exemplary dimensions are about 0.08 mm, about 0.1 mm and about 0.15 mm. Another exemplary dimension for incompressible element 50 is 2 mm.

To facilitate flow of sample fluid in sample chamber 55, incompressible element 50 may be hydrophilic. The entire incompressible element 50 may be hydrophilic, or element 50 may merely have a hydrophilic surface coating or treatment. The hydrophilic nature facilitates drawing aqueous sample, e.g., blood, into sample chamber 55, such as by facilitating wicking and/or by capillary action.

Specific examples of materials that are suitable for preparing incompressible element 50, include, but are not limited to, a multifilament material, such as, for example, an untreated, braided polyester thread typically used as suture material. A suitable untreated, braided polyester thread is commercially available from Pearsalls Limited (United Kingdom) as item number 35A103000, EP1 or US size 5/0. The diameter of this material ranges from 0.100 to 0.149 mm. Another material suitable for use as incompressible element 50 is a monofilament material typically used as fishing line, commercially available as "WBClarke Match Team", having a diameter of 0.08 mm and rating of 0.80 kg, readily available from sporting goods stores in the United Kingdom. Another suitable material is a ribbon having the trademark "MELINEX" from DuPont, typically 50 micrometers thick, slit to a width of 2 mm and wound on a bobbin.

In order to remain functional throughout a sensor's life, incompressible element 50 is able to resist being substantially deformed by the methods used to manufacture sensor strips 10 and also be able to resist being deformed under normal conditions of storage and use.

The dimensions of incompressible element 50 are specified by the size and shape of sample chamber 55 and the inlet opening 54 desired. Accordingly, simply by changing incompressible element 50 the size and/or shape of sample chamber 55 may be changed. The shape of the cross-section of incompressible element 50 may be any suitable shape, e.g., may be, but is not limited to, circular, elliptical, polygonal, typically regular polygonal, or irregular. FIGS. 3 through 6 show alternative incompressible elements, elements 50, 150, 50A, 50B, respectively, and varying shapes and sizes of inlets 54, 154, 54A, 54B.

Figure 4:
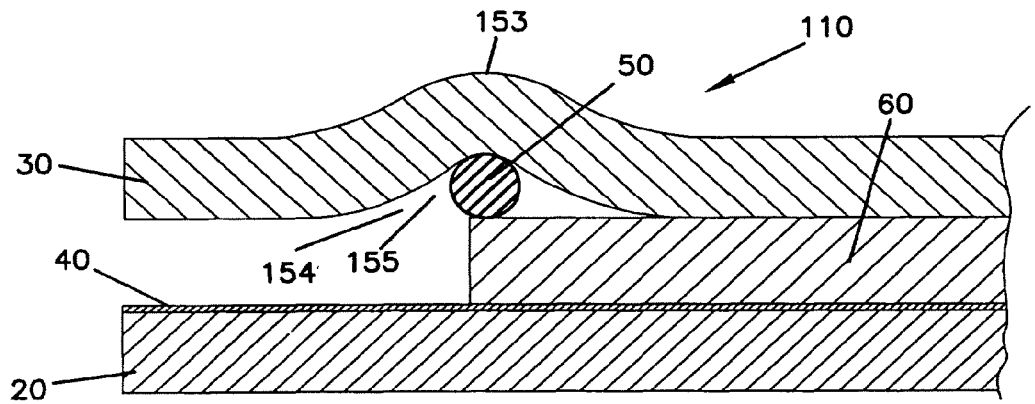
FIG. 4 is a cross-sectional view of another embodiment of a biosensor strip.
Figure 5:
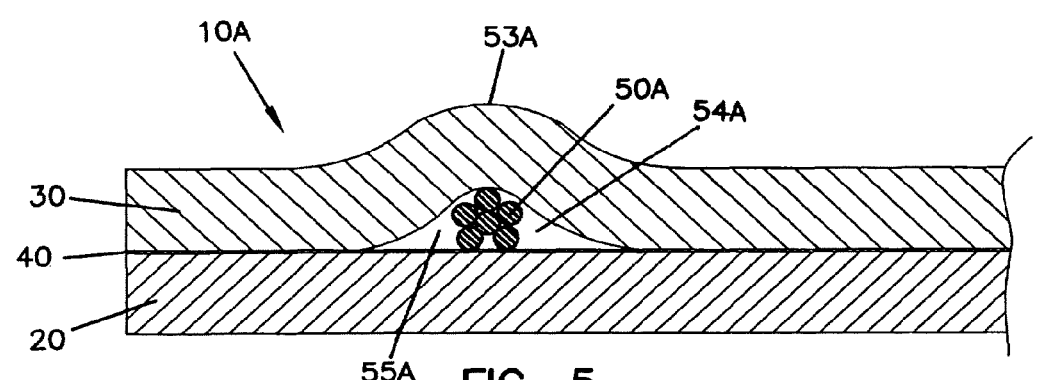
FIG. 5 is a cross-section view of another embodiment of a biosensor strip, the construction similar to that of FIG. 3.
Figure 6:
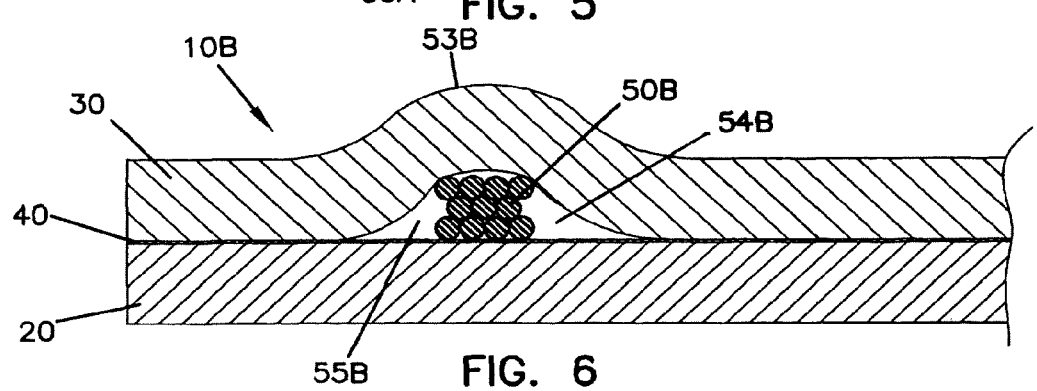
FIG. 6 is a cross-section view of another embodiment of a biosensor strip, the construction similar to that of FIG. 3.

Specifically, sensor 10 in FIG. 3 and sensor 110 in FIG. 4 include incompressible element 50, 150, respectively, as a monofilament. An alternate incompressible element is illustrated in FIG. 5, in which sensor 10A has sample chamber 55A formed by incompressible element 50A, a multifilament element, such as a thread, having a generally circular cross-section. Yet another incompressible element is illustrated in FIG. 6, where sensor 10B has sample chamber 55B formed between substrates 20, 30 by incompressible element 50B. Incompressible element 50B is a multifilament element, such as a ribbon, tape, or yarn, having a generally rectangular cross-section.

As can be seen in each of FIGS. 4 through 6, incompressible element 50, 150, 50A, 50B is sufficiently strong to hold up and deform substrate 30 without incompressible element 50, 150, 50A, 50B substantially misshaping itself. Indeed, typically substrate 30 is deformable and, as such, deforms due to the presence of incompressible element 50, 150, 50A, 50B, forming bump 53, 153, 53A, 53B, respectively, in a location proximate incompressible element 50, 150, 50A, 50B. The shape and size of bump 53, 153, 53A, 53B is generally dependent on the shape and size of incompressible element 50, 150, 50A, 50B. The thickness, flexibility, rigidity, etc. of substrate 30 may affect the size and shape of the resulting bump.

Optional Spacer Layer

As indicated above, positioned between substrate 20 and substrate 30 may be a spacer layer. FIG. 4 illustrates an embodiment in which sensor 110 includes spacer 60 present between substrate 20 and substrate 30. Spacer 60 separates first substrate 20 from second substrate 30, and, in this embodiment, incompressible element 50 is positioned on spacer 60. Together, substrates 20, 30, spacer 60 and incompressible element 50 form sample chamber 155.

Spacer 60 is an inert non-conducting substrate, typically at least as flexible and deformable (or as rigid) as substrates 20, 30. In certain embodiments, spacer 60 is an adhesive layer or double-sided adhesive tape or film. Any adhesive selected for spacer 60 should be selected to prevent or minimize diffusion or the release of material that may interfere with accurate analyte measurement.

In certain embodiments, the thickness of spacer 60 may be at least about 0.01 mm (10 µm) and no greater than about 1 mm or about 0.5 mm. For example, the thickness may be between about 0.02 mm (20 µm) and about 0.2 mm (200 µm). In one certain embodiment, the thickness is about 0.05 mm (50 µm), and about 0.1 mm (100 µm) in another embodiment. Spacer 60 is an inert, insulative layer. An example of a suitable material for spacer 60 is a double sided adhesive tape.

Electrode Arrangement

To perform an assay, sensor strip 10 includes electrode arrangement 50, which includes a plurality of electrodes. Electrodes suitable for comprising an electrode arrangement for a biosensor for this invention are well-known to those of ordinary skill in the art. In general, electrode arrangement 50 comprises a working electrode and a counter electrode, and optionally, any of a reference electrode, a trigger or indicator electrode, and/or auxiliary electrodes. A "working electrode" is an electrode at which analyte is electrooxidized or electroreduced. A "counter electrode" refers to an electrode, used in conjunction with a working electrode, through which passes an electrochemical current equal in magnitude and opposite in sign to the current passed through the working electrode. The term "counter electrode" is meant to include counter electrodes which also function as reference electrodes (i.e. a counter/reference electrode). A "reference electrode" includes a reference electrode that also functions as a counter electrode (i.e., a counter/reference electrode) unless the description provides that a "reference electrode" excludes a counter/reference electrode. An "indicator electrode" includes one or more electrodes that detect partial or complete filling of a sample chamber and/or measurement zone.

One suitable electrode arrangement 50 is illustrated in FIG. 2 on substrate 20. In this embodiment, electrode arrangement 50 includes one working electrode and two counter electrodes, specifically, working electrode 52 and counter electrodes 54, on substrate 20. Electrodes 52, 54 may be present directly on substrate 20 or may have a layer therebetween, such as an adhesive layer. In this embodiment, electrodes 52, 54 are co-planar, both being on the same substrate. The term "planar electrodes" or "co-planar electrodes" refers to a configuration of the working and counter electrodes in which the working surface of the working electrode is disposed at least approximately planar to a surface of the counter electrode. "Planar electrodes" or "co-planar electrodes" are typically located on the same substrate. It should be understood that other electrode configurations are possible and that fall within the scope of this invention. For example, a working electrode could be on substrate 20 and counter electrode on substrate 30; such a configuration would be facing electrodes. In general, the term "facing electrodes" refers to a configuration of the working and counter electrodes in which the working surface of the working electrode is disposed in approximate opposition to a surface of the counter electrode.

Working Electrode

Referring to FIG. 2, at least one working electrode is positioned on first substrate 20 or second substrate 30 in the region of sample chamber 55; in this embodiment, working electrode 42 is present on substrate 20. Working electrode 42 includes a conductive trace 46 extending to the proximal end, such as for connecting to a meter or other appropriate measurement device (not shown).

Working electrode 42 may be a layer of conductive material such as gold, carbon, platinum, ruthenium dioxide, palladium, or other non-corroding, conducting material. The material of working electrode 42 typically has relatively low electrical resistance and is typically electrochemically inert over the potential range of the sensor during operation. An example of a suitable conductive epoxy is ECCOCOAT CT5079-3 Carbon-Filled Conductive Epoxy Coating (available from W.R. Grace Company, Woburn, Mass.).

Working electrode 42 may be applied to substrate 20 by any of various methods. Electrode 42 may be deposited, such as by vapor deposition or vacuum deposition, sputtered, printed on a flat surface or in an embossed or otherwise recessed surface, transferred from a separate carrier or liner, etched, or molded. Screen-printing is a suitable method for applying working electrode 42, although other methods such as piezoelectric printing, ink jet printing, laser printing, photolithography, and painting may be used.

Working electrode 42 is provided in sample chamber 55 for the analysis of analyte, in conjunction with the counter electrode, as will be described below.

The trace 46 could optionally be overlaid with a layer of an electrically insulating material, to inhibit short circuits; however, working electrode 42 should not be covered by any layer of hydrophobic electrically insulating material.

Counter Electrode

Sensor strip 10 typically includes at least one counter electrode positioned within sample chamber 55 on either substrate 20, 30. Referring to FIG. 2, two counter electrodes 44 are illustrated on substrate 20. Each counter electrode 44 includes a conductive trace 48 extending to the proximal end, such as for connecting to a meter or other appropriate measurement device (not shown).

Counter electrode 44 may be constructed in a manner similar to working electrode 42. Counter electrode 44 may also be a counter/reference electrode. Alternatively, a separate reference electrode may be provided in the sample chamber. Suitable materials for the counter electrode, counter/reference or reference electrode include Ag/AgCl or Ag/AgBr applied (e.g., printed) on a non-conducting base material or silver chloride on a silver metal base. The same materials and methods may be used to make counter electrode 44 as are available for constructing working electrode 42, although different materials and methods may also be used. Counter electrode 44 may include a mix of multiple conducting materials, such as Ag/AgCl and carbon.

The trace 48 could optionally be overlaid with a layer of an electrically insulating material, to inhibit short circuits; however, counter electrode 44 should not be covered by any layer of hydrophobic electrically insulating material.

Optional Additional Electrodes

Sensor strip 10 may include additional electrodes in sample chamber 55. Examples of such optional additional electrodes include indicator electrode(s), reference electrode(s), and auxiliary electrode(s).

Indicator electrodes may be used to detect when sample chamber 55 has been sufficiently filled with sample, to prevent obtaining a measurement from a partially filled sample chamber or measurement zone. In some embodiments, such as the embodiment illustrated in FIG. 2 where a counter electrode 44 is present on each side of working electrode 42, one of counter electrodes 44 functions as an indicator electrode to detect sufficient filling.

Any optional electrode(s) may be constructed in a manner similar to working electrode 42 and/or counter electrode 44. Suitable materials and methods for these electrodes include the same materials and methods as used for working electrode 42 and/or counter electrode 44, although different materials and methods may also be used.

Sensing Chemistry

To facilitate the analysis of the analyte, sensing chemistry is provided in sample chamber 55 proximate electrode arrangement 40. Sensing chemistry facilitates the transfer of electrons between electrode arrangement 40, generally working electrode 42, and the analyte in the sample. Any suitable sensing chemistry may be used in sensor strip 10; the sensing chemistry may include one or more materials. As will be apparent to those of skill in the art, the particulars of the sensing chemistry will depend at least in part on the analyte(s) intended to be assayed. For example, in certain embodiments, a sensor may be a glucose sensor and the sensing chemistry is selected for assaying glucose. Sensors of the subject invention may be adapted to assay for analytes other than glucose. For example, analytes that may be assayed include, but are not limited to, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Any or all of the sensing chemistry may be diffusible or leachable, or non-diffusible or non-leachable. For purposes of discussion herein, the term "diffusible" will be used to represent "diffusible or leachable" and the term "non-diffusible" will be used to represent "non-diffusible or non-leachable" and variations thereof. A "non-diffusible," "non-leachable," or "non-releasable" compound is a compound which does not substantially diffuse away from the surface on which it is present for the duration of the analyte assay.

In certain embodiment, sensing chemistry is provided via incompressible element 50, present on the surface thereof or impregnated into, and optionally throughout, element 50. In many embodiments, the sensing chemistry is coated into and/or onto incompressible element 50 by a solution, generally prior to incorporation into sensor 10.

Electron Transfer Agent

The sensing chemistry generally includes an electron transfer agent that facilitates the transfer of electrons to or from the analyte. The electron transfer agent may be diffusible or non-diffusible, and may be present on working electrode 42 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes may be used for other analytes.

The electron transfer agent, whether it is diffusible or not, facilitates a current between working electrode 42 and the analyte and enables the electrochemical analysis of molecules. The agent facilitates the transfer electrons between the electrode and the analyte.

Redox Mediator

The sensing chemistry may, additionally to or alternatively to the electron transfer agent, include a redox mediator. A redox mediator is an agent for carrying electrons between the analyte and the working electrode, either directly, or via an electron transfer agent. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator may be a polymeric redox mediator, or, a redox polymer (i.e., a polymer having one or more redox species). Examples of suitable redox mediators and redox polymer are disclosed in U.S. Pat. No. 6,338,790, for example, and in U.S. Pat. Nos. 6,605,200 and 6,605,201.

If the redox mediator is non-diffusible, then the redox mediator may be disposed on working electrode 42 as a layer. In an embodiment having a redox mediator and an electron transfer agent, if the redox mediator and electron transfer agent are both non-leachable, then both components are disposed on working electrode 42 as individual layers, or combined and applied as a single layer.

The redox mediator, whether it is diffusible or not, mediates a current between working electrode 42 and the analyte and enables the electrochemical analysis of molecules which may not be suited for direct electrochemical reaction on an electrode. The mediator functions as an agent to transfer electrons between the electrode and the analyte.

Operation of the Sensor Strip

In use, a sample of biological fluid is provided into the sample chamber of the sensor, where the level of analyte is determined. A "biological fluid" is any body fluid in which the analyte can be measured, for example, blood, interstitial fluid, dermal fluid, sweat, tears, and urine. "Blood" includes whole blood and its cell-free components, such as, plasma and serum. In many embodiments, it is the level of glucose in blood or interstitial fluid that is determined. The sensors of the present invention may be adapted and used to determine the presence of analytes other than glucose, as will be apparent to those of skill in the art and as described herein. Also in many embodiments, the source of the biological fluid is a drop of blood drawn from a patient, e.g., after piercing the patient's skin with a lancing device or the like, which may be present in an integrated device, together with the sensor strip.

Embodiments of the subject methods may include contacting the sensor (e.g., an overhang of the sensor) with a fluid sample (obtained, e.g., from a skin incision) and transferring a volume of the fluid to the sample chamber of the sensor. Accordingly, bodily fluid may be first contacted with at least a portion of one of the substrates of the sensor (e.g., the overhang of a top substrate) prior to being contacted with the other substrate and/or sample chamber.

Application of the Sensor

A common use for an analyte sensor of the present invention, such as sensor strip 10, is for the determination of analyte concentration in a biological fluid, such as glucose concentration in blood, interstitial fluid, and the like, in a patient or other user. Sensor strips 10 may be available at pharmacies, hospitals, clinics, from doctors, and other sources of medical devices. Multiple sensor strips 10 may be packaged together and sold as a single unit; e.g., a package of 25, 50, or 100 strips.

Sensor strips 10 may be used for an electrochemical assay, or, for a photometric test. Sensor strips 10 are generally configured for use with an electrical meter, which may be connectable to various electronics. A meter may be available at generally the same locations as sensor strips 10, and sometimes may be packaged together with sensor strips 10, e.g., as a kit.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touchscreen. With such an arrangement, the user can control the meter indirectly by interacting with the user interface(s) of the server device, which in turn interacts with the meter across a wireless link.

The server device can also communicate with another device, such as for sending data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as sensor strips 10 and the meter, and sometimes may be packaged together with sensor strips 10 and/or meter, e.g., as a kit.

Sensor strips 10 are particularly suited for inclusion in an integrated device, i.e., a device which has the sensor and a second element, such as a meter or a lancing device, in the device. The integrated device may be based on providing an electrochemical assay or a photometric assay. In some embodiments, sensor strips 10 may be integrated with both a meter and a lancing device. Having multiple elements together in one device reduces the number of devices needed to obtain an analyte level and facilitates the sampling process. For example, embodiments may include a housing that includes one or more of the subject strips, a skin piercing element and a processor for determining the concentration of an analyte in a sample applied to the strip. A plurality of strips 10 may be retained in a cassette in the housing interior and, upon actuation by a user, a single strip 10 may be dispensed from the cassette so that at least a portion extends out of the housing for use.

Manufacture of the Sensors

Sensor strips 10 are sandwiched or layered constructions having substrates 20, 30 with incompressible element 50 present therebetween. Such a construction may be made by laminating the various layers together, in any suitable manner. Various suitable methods are generally outlined below.

A continuous method may be used to make sensors 10, including applying substrate 30, having a layer of an adhesive, onto substrate 20 having electrode arrangement 40 and incompressible element 50 previously positioned thereon. Sensors 10 may be formed from segments of substrates or from sheets or webs of substrate, which are later cut or slit to provide individual sensors 10. A hot melt or heat activatable adhesive could be used to adhere substrates 20, 30 to the remaining components of biosensor strip 10. Such a method may include providing a plurality of uncompleted biosensor strips, such as in a row; providing a substrate having a backing bearing a layer of adhesive on one major surface thereof; providing a length of material suitable for forming incompressible elements; combining the substrate and the length of material for forming incompressible elements, whereby the substrate and the length of material for forming the incompressible elements form an assembly; feeding the row into a substrate application apparatus, e.g., a laminator; feeding the assembly into the substrate application apparatus, e.g., laminator; applying the assembly to the row, e.g., by lamination, whereby the row contains a plurality of completed biosensor strips; and separating the row of completed biosensor strips to provide a plurality of individual biosensor strips. If the adhesive is a hot melt adhesive, the substrate is preheated on a substrate application apparatus prior to being combined with the incompressible element, and the resulting combination of the substrate and incompressible element applied to the remaining components of the biosensor strip. If the adhesive is a pressure-sensitive adhesive, there is no need to preheat the substrate on a tape application apparatus prior to combining the substrate and the incompressible element and applying the resulting combination to the remaining components of the biosensor strip.

Details for various methods of manufacturing sensors are discussed, for example, in co-pending application having Ser. No. 11/147,532, having inventors Petyt, Savage, and Hector, which is commonly assigned to Abbott Diabetes Care, Inc.

The invention has been described with reference to various embodiments and techniques. However, it will be apparent to one of ordinarily skill in the art that many variations and modifications may be made while remaining within the spirit and scope of the invention.

All patents, applications and other references in this specification are indicative of the level of ordinary skill in the art to which this invention pertains.

What is claimed is:

1. A biosensor comprising:
a first substrate and a second substrate;
a spacer layer positioned in between the first substrate and the second substrate;
a sample chamber positioned between the first substrate and the second substrate, the sample chamber having only two openings;
an incompressible element positioned within a portion of the sample chamber, wherein the incompressible is a monofilament, a thread or a yarn;
wherein the biosensor comprises a proximal end and a distal end, a first side extending between the proximal end and the distal end of the biosensor, and a second side extending between the proximal end and the distal end of the biosensor, and wherein the incompressible element extends from an edge of the first side to an edge of the second side of the biosensor and provides the two openings in the sample chamber,
wherein the first substrate is deformable and deforms due to the incompressible element.

2. The biosensor of claim 1, further comprising sensing chemistry proximate the incompressible element.

3. The biosensor of claim 2, wherein the sensing chemistry comprises an enzyme.

4. The biosensor of claim 3, wherein the enzyme comprises glucose oxidase or glucose dehydrogenase.

5. The biosensor of claim 2, wherein the sensing chemistry further comprises a redox mediator.

6. The biosensor of claim 5, wherein the redox mediator comprises a transition metal compound or complex.

7. The biosensor of claim 6, wherein the transition metal compound or complex comprises osmium, ruthenium, iron, or cobalt compound or complex.

8. The biosensor of claim 1, wherein the sample chamber has a volume of no more than about 1 microliter.

9. The biosensor of claim 8, wherein the sample chamber has a volume of no more than about 0.5 microliter.

10. The biosensor of claim 8, wherein the sample chamber has a volume of no more than about 0.1 microliter.

11. The biosensor of claim 1, wherein the spacer layer comprises an adhesive layer.

12. The biosensor of claim 11, wherein the adhesive layer is a double-sided adhesive tape.

13. The biosensor of claim 11, wherein the adhesive layer is a double-sided adhesive film.

14. The biosensor of claim 1, wherein the sample chamber comprises an electrode arrangement comprising a working electrode and a counter electrode.

15. The biosensor of claim 14, wherein the sample chamber further comprises a reference electrode.

16. The biosensor of claim 14, wherein the working electrode and counter electrode are placed on the first substrate.

17. The biosensor of claim 14, wherein the working electrode and counter electrode are placed on the second substrate.

18. The biosensor of claim 14, wherein the working electrode is placed on the first substrate and the counter electrode is placed on the second substrate.

19. The biosensor of claim 14, wherein the sample chamber further comprises an indicator electrode.

20. The biosensor of claim 19, wherein the counter electrode is present on one side of the working electrode and indicator electrode is present on the other side of the working electrode.

* * * * *